United States Patent [19]
Salkin

[11] 3,997,679
[45] Dec. 14, 1976

[54] STABILIZATION OF XANTHOPHYLLS
[75] Inventor: Ralph Salkin, Kinnelon, N.J.
[73] Assignee: CPC International Inc., Englewood Cliffs, N.J.
[22] Filed: Aug. 12, 1974
[21] Appl. No.: 496,489
[52] U.S. Cl. .............................. 426/250; 426/540; 426/635; 426/807; 260/236.5; 260/410
[51] Int. Cl.$^2$ ..................... A23L 1/275; A23K 1/16
[58] Field of Search ............... 426/1, 21, 807, 177, 426/250, 540, 635; 260/236.5, 410

[56] References Cited
UNITED STATES PATENTS

| 3,523,138 | 8/1970 | Grant | 426/807 |
| 3,535,426 | 10/1970 | Hawks | 426/177 |

FOREIGN PATENTS OR APPLICATIONS

| 630,670 | 11/1961 | Canada | 426/807 |

Primary Examiner—Jeanette M. Hunter
Attorney, Agent, or Firm—Salvatore C. Mitri

[57] ABSTRACT

The xanthophyll esters, that are normally recovered from plant sources such as the marigold plant, *Tagetes erecta*, are selectively saponified. The neutralized, selectively saponified material, when incorporated into an inert carrier, provides a stable xanthophyll product having a pH above about 8. Such products have improved stabilities as compared to the original esters or to fully saponified esters.

10 Claims, No Drawings

STABILIZATION OF XANTHOPHYLLS

INTRODUCTION

This invention relates to xanthophyll compositions, for use in feeds, particularly poultry feeds, that are characterized by greatly improved stability.

BACKGROUND

Grant, in U.S. Pat. No. 3,523,138 granted Aug. 4, 1970, described the treatment of xanthophylls with aqueous alkali materials. The result was said to be an increase in the pigmenting activity. The alkali-treated xanthophyll material was used as such, or dispersed in vegetable oil, or incorporated into a dry product such as, for example, calcium silicate, soybean meal, saturated fat material, gelatin, or starch. The treated xanthophyll, whether in a concentrate, a dispersion, or in a solid product, was then incorporated in poultry feed for increasing pigmentation activity.

A later U.S. Pat. No. 3,535,426 described the technique of mixing an alkali-treated xanthophyll material with a large amount of a fatty acid, which served as a carrier. The very high quantities of fat employed were said to increase the stability of the product.

OBJECTS OF THE PRESENT INVENTION

One object of the present invention is to provide novel xanthophyll compositions characterized by greatly improved stability.

A related object of the invention is to provide a practical process for preparing xanthophyll compositions, particularly adapted for use in poultry feeds, and characterized by enhanced stability.

BRIEF SUMMARY OF THE INVENTION

Enhanced stability of xanthophyll esters is observed when the esters are partially saponified, then neutralized with a weak acid, so that the final product contains up to 50% of the esters that are not saponified, and has a pH above 8. Optimum stability is apparently obtained when saponification is about 85% complete.

DESCRIPTION OF THE INVENTION

The xanthophyll esters are thought to owe their color to the presence of multiple conjugated double bonds. They are not stable products, and are rapidly lost from poultry feeds by oxidation.

The xanthophyll esters have no nutrient value. However, they are important in other ways, in poultry feeds. When ingested, they produce a yellow coloration of the skin, shanks and body fat that enhances the marketability of the chickens. In the case of laying hens, xanthophylls in the feed produce a highly yellow-pigmented egg yolk that is much sought after for the manufacture of mayonnaise, noodles, and the like, imparting a full-bodied golden appearance to these consumer products.

Practical sources of xanthophyll esters, for use in poultry feeds, are yellow corn and corn gluten meal. However, these xanthophyll sources vary in their xanthophyll content, and cannot be relied upon. Marigold flowers and petal meal contain many times the xanthophyll content of yellow corn and provide a highly concentrated source of biologically available xanthophyll esters.

Unfortunately, the amount of xanthophyll that is present in marigold flowers and petals, when harvested, decreases rapidly upon drying, milling, and storing, as well as after mixing with other ingredients to make a poultry feed. Moreover, destructive oxidative loss of xanthophyll esters not only occurs on storage but also in the intestine after ingestion or even after absorption.

To make more stable products, xanthophyll esters are treated first with alkali. The alkaline material may be in the form of alcoholic potassium hydroxide or sodium hydroxide. The xanthophyll esters, generally in the form of an extract, are treated with the alcoholic alkali at reflux temperature, under nitrogen, to effect an incomplete selective saponification of the xanthophyll esters. The reaction mixture is then stabilized by the addition of an antioxidant and the free alkali is taken up by the addition of a weak organic acid. The resulting product can be used as such or mixed with a carrier, in a fashion well known in the art, to form a dry, free-flowing stable xanthophyll concentrate.

More specifically, in accordance with one preferred embodiment of the invention, xanthophyll esters are refluxed with alcoholic potassium hydroxide under nitrogen to effect partial saponification. Thereafter, a methylene chloride solution containing the antioxidant material, ethoxyquin, and a weak organic acid, is added with stirring at 45° C–50° C, until essentially all of the solids have been dissolved. The resulting solution is then mixed with a suitable carrier, and dried under vacuum at 45° C to 50° C, to produce the dry, free-flowing stable product. Xanthophyll concentrates produced in accordance with the present invention are quite amenable to incorporation in poultry feeds.

An especially desirable marigold extract, for use in the present invention, is that derived from the marigold plant *Tagetes erecta*. The carotenoid esters contained in the species comprise at least about 70% of lutein equivalent, and smaller proportions of zeaxanthin and beat-cryptoxanthin. In most instances the lutein content of the xanthophylls is from about 75% to about 90%.

The partial saponification should be conducted so that saponification is less than complete, but is at least 50% complete. The alkali treatment step, that accomplishes the partial saponification, is conveniently performed at reflux under anhydrous conditions. The temperature therefore generally does not exceed 150° C, and ordinarily will be less than 100° C.

The alkali treatment is easily accomplished by mixing the xanthophyll esters, which may be, for example, in the form of xanthophylls extracted from marigold petal meal, with alkali, preferably in the presence of a suitable organic polar liquid, such as a lower alkanol. Suitable alkali materials include such inorganic basic materials such as the alkali metal hydroxides, such as sodium hydroxide and potassium hydroxide.

The degree to which saponification has been completed can be determined by thin layer chromatography (TLC) as well as by spectrophotometric methods. When the saponification is complete, stabilities are markedly poorer than when the xanthophyll esters are processed in accordance with the present invention. Poorer stabilities are also observed when completely saponified materials are mixed with other materials, thus demonstrating the direct connection between partial saponification and improved stability.

The amount of caustic that is required to achieve the desired less-than-complete saponification appears to bear little or no relationship to the saponification number of a given xanthophyll extract. For convenience hereafter, the amount of caustic employed in any particular case is described by weight, and also in terms of its ratio to the total amount of xanthophylls present, in the extract.

The quantity of caustic required to effect the desired degree of saponification can be determined in advance from small representative samples and is best expressed by a ratio of the grams of alkali/grams of xanthophylls, which generally will be in the range of 0.30–0.50 when the alkali is potassium hydroxide. The preferred degree of saponification is at least about 50%, the more preferred degree of saponification is at least 75%, and optimum results are observed when saponification is only about 85% complete. However, a preferred range of saponification is 80% to 90% of completion, or in other words, the end product should contain from about 10% to about 20% by weight of the unsaponified original xanthophyll esters.

The amount of caustic used is less than stoichiometric, based on the saponification number, which results in only very small amounts of free alkali remaining after completion of the saponification step. Weak acids such as acetic, propionic, or lauric, for example, can be used to neutralize the residual alkali to produce a pH of about 8, preferably 9.0–9.5, in the finished formulation. For example, the stearic acid level used need only be 0.5 to 2 times the xanthophylls content.

In one comparative demonstration of the invention, a Tagetes extract containing 12.5% xanthophyll esters was saponified in two portions to the free xanthophyll alcohol state to a degree comprising 85% and 100% selective hydrolysis, respectively. After 75 days storage at 40° C, finished formulations produced from these hydrolysates showed 5.2% and 37% loss of xanthophyll potency respectively, demonstrating the clear superiority of selective, incomplete saponification.

The following table presents another demonstration of comparative stability in the form of data from three types of formulations wherein the natural xanthophyll esters are unsaponified, partially saponified and completely saponified. All formulations contained an antioxidant combination consisting of 50% butylated hydroxytoluene (BHT) by weight and 50% ethoxyquin by weight, based on 100% xanthophyll content.

| Saponification | Percent Xanthophyll Loss Days at 40° C | | | | | | |
|---|---|---|---|---|---|---|---|
| | 8 | 16 | 32 | 44 | 60 | 72 | 85 |
| None | 0.9 | 4.6 | 6.4 | 7.4 | 11.9 | n.a. | 17.4 |
| Incomplete | 0.0 | n.a.* | 0.0 | n.a. | 0.0 | 3.2 | n.a. |
| Complete | 8.8 | 15.5 | 23.0 | 26.3 | 30.0 | n.a. | 35.0 |

*no assay

As starting material for this invention crude or partially purified extracts of Tagetes may be used. The alkali may be either sodium or potassium hydroxide, and the solvent, as vehicle for the reaction mixture, may be selected from the class of lower molecular weight aliphatic alcohols, e.g., methanol, ethanol or isopropanol.

While the alkali employed is preferably sodium hydroxide or potassium hydroxide, other basic materials may be employed, provided they are substantially equivalent. Similarly, while acetic acid and stearic acid are the acids of choice, other weak acids may also be used provided they are compatible with the other reactants and result in an edible product.

Likewise, one or more antioxidants may be used to inhibit oxidation. These can be added to the xanthophyll extract prior to treatment, during treatment or after treatment. Examples of suitable antioxidants include butylated hydroxyanisole (BHA), BHT, ethoxyquin, the tocopherols and lecithin.

The invention will now be further exemplified and demonstrated by descriptions of several specific examples. All references in the examples and elsewhere to parts and percentages are by weight, dry basis, unless otherwise specifically expressed in some other manner.

EXAMPLE 1

Stabilization of Xanthophylls from Partially Purified Extracts of *Tagetes Erecta*

To 200 grams of *Tagetes erecta* extract containing 12.5% xanthophylls (Xa) was added 250 ml. of methanolic KOH solution containing 8.7 grams of KOH (KOH/Xa ratio: 0.35). The mixture was refluxed under nitrogen for two hours with agitation.

To the partially cooled solution was added 12.5 grams of ethoxyquin and 12.5 grams of stearic acid dissolved in 150 ml. of methylene chloride. The well-mixed solution was then gradually incorporated into 200 grams of an inert carrier, calcium silicate. The moist powder was dried at 45° C–50° C in vacuo to yield 406 grams of a free-flowing xanthophyll (Xa) powder containing 5.6% Xa.

Thin layer chromatography showed 85% of this to be in the unesterified form. The pH of the product was 9.1. Upon 40° C storage for 75 days it showed a minimal 5.2% loss of xanthophylls.

EXAMPLE 2

Stabilization of Xanthophylls from Partially Purified Extracts Of *Tagetes Erecta*

To 50 grams of *Tagetes erecta* extract containing 26.9% xanthophylls (as determined by the AOAC method) was added a solution of 7.5 grams KOH (USP pellets) in 125 ml. of anhydrous methanol (KOH/Xa ratio: 0.56). The mixture was refluxed under nitrogen for 20 minutes with efficient agitation.

To the cooled solution was added 4.75 ml. of glacial acetic acid and 6.7 grams of ethoxyquin in 30 ml. of methylene chloride. The well-mixed solution was added slowly to 50 grams of an inert carrier, and mixed to accomplish a uniform distribution. The mix was then dried at 45° C–50° C in vacuo, yielding 115 grams of a concentrate containing 11.1% xanthophylls.

This layer chromatography showed the saponification to be about 80% complete. Upon storage at 40° C for 72 days, the xanthophyll loss was a minimal 6.3%.

EXAMPLE 3

Stabilization of Xanthophylls from Partially Purified Extracts of *Tagetes erecta*

To 200 grams of *Tagetes erecta* extract having a saponification number of 105, and containing 10.4% xanthophylls, was added 250 ml. of anhydrous ethanolic KOH containing 9.3 grams KOH (KOH/Ka ratio: 0.45). The mixture was refluxed under nitrogen for two hours with efficient agitation.

To the partially cooled mixture was added 150 ml. of methylene chloride containing 10.4 grams of ethoxyquin and 10.4 grams of stearic acid. The solution was added to 175 grams of an inert carrier, calcium silicate.

The moist mix was dried in vacuo at 45°-50° C to yield 397 grams of concentrate containing 5.08% xanthophylls, of which 30% was unsaponified, as determined spectrophotometrically.

The pH of the product was 9.5. Upon storage at 40° C for 65 days the product lost 11% xanthophylls.

EXAMPLE 4

Stabilization of Xanthophylls from Partially Purified Extracts of *Tagetes erecta*

To 201 grams of a *Tagetes erecta* AOAC assaying 11.2% xanthophylls was added a solution of 10.6 grams of KOH (KOH/Xa ratio: 0.475) in 250 ml. of technical anhydrous isopropanol. The mixture was refluxed under nitrogen for two hours with efficient agitation.

To the cooled solution was added a methylene chloride solution containing 5.6 grams of ethoxyquin and 11.2 grams of stearic acid. The solution was added slowly to 175 grams of an inert carrier and dried at 45° C–50° C in vacuo.

The yield was 405 grams of a product at a pH of 8.7, assaying 5.0% xanthophylls, 35% of which were in the unhydrolyzed ester form. Upon storage for 76 days at 40° C the xanthophylls loss was 1.0%.

EXAMPLE 5

Stabilization of Xanthophylls from Partially Purified Extracts of *Tagetes erecta*

To 200 grams of a *Tagetes erecta* extract with a saponification number of 101, and containing 11.2% xanthophylls (AOAC method), was added 250 ml. of methanolic KOH containing 10.6 grams of KOH (KOH/Xa ratio: 0.48). The mixture was refluxed under nitrogen for two hours with efficient agitation.

To the partially cooled solution was added 150 ml. of methylene chloride solution containing 11.2 grams of stearic acid and 11.2 grams of ethoxyquin. The well-mixed saponification solution was then incorporated into 180 grams of an inert carrier and dried at 45° C–50° C in vacuo.

The yield was 408 grams of a product containing 5.15% xanthophylls, of which about 90% was in the unesterified form. The product had a pH of 9.1, and under accelerated aging conditions at 40° C showed no loss at 77 days.

EXAMPLE 6

Prior Art Preparation of Xanthophylls from Partially Purified Extracts of *Tagetes erecta*

The following example is provided to demonstrate the instability of a completely saponified product.

To 200 grams of *Tagetes erecta* extract containing 12.5% xanthophylls was added 250 ml. of a methanolic KOH solution containing 10 grams of KOH (KOH/Xa ratio: 0.40). The mixture was refluxed under nitrogen for two hours. The saponification solution was diluted with 150 ml. of methylene chloride containing 12.5 grams of ethoxyquin and 12.5 grams of stearic acid and incorporated into 180 grams of an inert carrier.

The yield was 415 grams of product containing 5.8% xanthophylls. Thin layer chromatography indicated 100% saponification of the xanthophylls present. This material, when stored for 80 days at 40° C, showed a 37% loss.

CONCLUSION

While the invention has been described in connection with specific embodiments thereof, it will be understood that it is capable of further modification, and this application is intended to cover any variations, uses, or adaptations of the invention following, in general, the principles of the invention and including such departures from the present disclosure are come within known or customary practice in the art to which the invention pertains and as may be applied to the essential features hereinbefore set forth, and as fall within the scope of the invention.

I claim:

1. A stabilized xanthophyll product derived from marigolds in which the xanthophyll esters are partially saponified and which contains unsaponified xanthophyll esters in an amount of from about 10% up to no more than about 50% by weight of the original xanthophyll esters, said product having a pH of at least about 8.

2. A stabilized xanthophyll product in accordance with claim 1 wherein the amount of unsaponified xanthophyll esters are about 10% to 20% by weight of the original xanthophyll esters.

3. A stabilized xanthophyll product in accordance with claim 1 that has a pH in the range from 9 to 9.5.

4. A poultry feed containing, as a poultry pigmenting material, a stabilized xanthophyll product comprising partially saponified xanthophyll esters containing unsaponified xanthophyll esters in an amount of from about 10% up to no more than about 50% by weight of the original xanthophyll esters, said stabilized xanthophyll product having a pH of at least about 8.

5. A poultry feed in accordance with claim 4 wherein the unsaponified xanthophyll esters are in an amount of about 10% to 20 % by weight of the original xanthophyll esters.

6. A poultry feed in accordance with claim 4 wherein the pH is in the range from 9 to 9.5.

7. A process for obtaining a stabilized xanthophyll product comprising:
    mixing xanthophyll esters with an alkali metal hydroxide at reflux temperatures in the presence of a lower alkanol and under anhydrous conditions until said xanthophyll esters are saponified to an extent of at least about 50% by weight of the original xanthophyll esters;
    cooling said xanthophyll ester mixture and adding to said mixture a weak acid selected from the group consisting of acetic acid, proprionic acid and lauric acid until the pH of said mixture is at least about 8.0; and,
    drying said cooled mixture to obtain a stabilized xanthophyll production in the form of a free-flowing powder.

8. The process of claim 7 wherein the alkali metal hydroxide is a member selected from the group consisting of sodium hydroxide and potassium hydroxide and the lower alkanol is a member selected from the group consisting of methanol, ethanol and isopropanol.

9. The process of claim 7 wherein said alkali metal hydroxide is present in an amount of about 0.30–0.50 grams per gram of said original xanthophyll esters.

10. A process in accordance with claim 7 wherein the pH of the final product is in the range from 9 to 9.5.

* * * * *